United States Patent [19]
Caligiuri et al.

[11] Patent Number: 6,042,826
[45] Date of Patent: Mar. 28, 2000

[54] METHOD FOR INDUCING APOPTOSIS OF PRIMARY CENTRAL NERVOUS SYSTEM B CELL LYMPHOMAS

[75] Inventors: Michael A. Caligiuri; Robert B. Baiocchi, both of Columbus, Ohio

[73] Assignee: Health Research, Inc., Buffalo, N.Y.

[21] Appl. No.: 08/969,881

[22] Filed: Nov. 14, 1997

Related U.S. Application Data

[60] Provisional application No. 60/030,956, Nov. 15, 1996.
[51] Int. Cl.[7] ......................... A61K 39/395; A61K 38/16; C12P 21/08; C07K 16/00
[52] U.S. Cl. ..................................... 424/130.1; 424/133.1; 424/135.1; 424/143.1; 424/144.1; 424/85.1; 424/85.2; 424/85.4; 530/387.3; 530/388.1; 530/388.22; 514/12
[58] Field of Search ............................... 424/130.1, 133.1, 424/135.1, 143.1, 85.1, 85.2, 85.4, 144.1; 530/387.3, 388.1, 388.22; 514/12

[56] References Cited

PUBLICATIONS

Leithauser et al., "Constitutive and Induced Expression of APO–1 . . ." Laboratory Investigation, 1993, vol. 69, No. 4, p. 415.

Dhein et al., "Induction of Apoptosis by Monoclonal Antibody Anti–APO–1 Class Switch Variants is Dependent on Cross–Linking of APO–1 Cell Surface Antigens", The Journal of Immunology, 1992, vol. 149, No. 10, p. 3166.

*Primary Examiner*—Sheela Huff
*Assistant Examiner*—Geetha P. Bansal
*Attorney, Agent, or Firm*—Hodgson, Russ, Andrews, Woods & Goodyear LLP

[57] ABSTRACT

A method for treating a primary central nervous system lymphoma in an individual relates to administering intrathecally or intralesionally a therapeutically effective amount of a Fas-cross-linking composition thereby inducing the lymphoma cells to undergo Fas-mediated cytotoxicity. The Fas-cross-linking composition may be an agonist antihuman Fas monoclonal antibody or fragments thereof, soluble Fas-ligand (Fas-L), and a combination thereof. In another embodiment, the lymphoma is pretreated with a composition that enhances Fas-mediated cytotoxicity induced by a Fas-cross-linking composition, followed by treatment with the Fas-cross-linking composition.

22 Claims, 3 Drawing Sheets

METHOD FOR INDUCING APOPTOSIS OF PRIMARY CENTRAL NERVOUS SYSTEM B CELL LYMPHOMAS

This application claims the priorty of co-pending provisional application U.S. Ser. No. 60/030,956, filed Nov. 15, 1996 which is incorporated herein by reference.

This invention was made with government support under grants CA09581, 9403-80 and CA65670 awarded by the National Institutes of Health. The government has certain rights in the invention.

FIELD OF THE INVENTION

The present invention is related to novel methods for anticancer therapy of certain tumor types in humans. More particularly, the present invention is related to the methods for the induction of apoptosis of primary central nervous system B cell lymphomas.

BACKGROUND OF THE INVENTION

1. Apoptosis

Regulation of cell number is determined by a balance between cell proliferation and cell death. One general mechanism of cell death seen in the process of development, differentiation, and cell turnover is apoptosis. Apoptosis is a characteristic form of cell death involving activation of one or more internally controlled pathways leading to autodigestion. Characteristic changes typical of a cell undergoing apoptosis include cell shrinkage and loss of contact with neighboring cells, cytoskeletal disruption, membrane blebbing and alterations in the plasma membrane, and endonuclease activity-associated degradation of DNA. There are various inducers of apoptosis including: physiologic activators such as TNF, Fas ligand, transforming growth factor β, certain neurotransmitters, calcium, and glucocorticoids; damage-related inducers such as heat shock, viral infection, bacterial toxins, tumor suppressors, and free radicals; therapeutic agents such as chemotherapeutic agents (cisplatin, doxorubicin, bleomycin, etc.), and gamma radiation; and toxins such as β-amyloid peptide.

Apoptosis can be induced by the binding and cross-linking of a cell surface receptor known as Fas. Human Fas (also known as APO-1 and CD95) is a cell surface protein consisting of 325 amino acids with a signal sequence at the $NH_2$-terminus and a membrane spanning region in the middle of the molecule. Fas appears to be constitutively expressed on cells of a varied, but limited, number of normal tissues, including skeletal muscle, liver, skin, heart, lung, kidney, and reproductive tissues (Leithauser et al., 1993, *Laboratory Invest.* 69:415; Watanabe-Fukunaga et al., 1992, *J. Immunol.*, 148:1274). Malignant cells of hematologic or nonhematologic origin have been analyzed for Fas expression (See, e.g., Leithauser et al., 1993, supra). Of relevance to the present invention, for example, a minority (approximately 15%) of B cell chronic lymphocytic leukemia cells (CLL) express the Fas antigen (Panayiotidis et al., 1995, *Leukemia* 9:1227–32); only one of eight B-cell lymphomas expressed Fas antigen which was at a very low level (Owen-Schaub et al., 1993, *J. Inmmunother.* 14:234–41); and only one of eight Burkitt's lymphoma expressed Fas antigen (Leithauser et al., 1993, supra).

Fas-mediated apoptosis requires cross-linking of Fas with either agonistic anti-Fas antibody, with cell bound FasL (Fas-ligand), or with soluble FasL (see, e.g. Alderson et al., 1995, *J. Exp. Med.* 181:71–77; Yonehara et al., 1989, *J. Exp. Med.* 169:1747–1756; Suda et al., 1994, *J. Exp. Med.* 179:873). However, the response to Fas cross-linking on Fas-bearing cells is variable. For example, resistance to Fas-mediated apoptosis after anti-Fas antibody treatment has been observed in some myeloma cells (Westendorf et al., 1995, *Blood* 85:3566–76), B-cell and T-cell lymphomas (Owen-Schaub et al., 1993, supra), and CLL (Panayiotidis et al., 1995, supra). Thus, the fact that a cell may bear Fas antigen does not necessarily confer sensitivity of that cell to anti-Fas mediated cytotoxicity.

2. Primary Central Nervous System Lymphomas (PCNSL)

PCNSL, an intracranial malignant lymphoma, involves the brain parenchyma, meninges, and rarely, the eye. While occurrence of PCNSL was relatively uncommon, the incidence of PCNSL continues to rise among patients afflicted with AIDS, and among patients receiving allogenic solid organ or bone marrow transplantation. For example, it is estimated that 2% to 6% of AIDS patients will develop clinical evidence of PCNSL; and that at autopsy, up to 11% will have occult PCNSL (Schultz et al., 1996, *J. Clin. Oncol.* 14:556–564). An intrinsic feature of PCNSL is resistance to standard therapeutic regimens. Radiation therapy, the primary therapy currently used, typically results in a high failure rate; and radiation combined with chemotherapy (cyclophosphamide, doxorubicin, vincristine, and dexamethasone) does not significantly improve survival amongst treated patients (Schultz et al., 1996, supra). Lack of an effective therapy contributes towards the poor prognosis of patients with this malignancy. In that regard, life expectancy of an immuno-suppressed patient having PCNSL is approximately 2 to 4 months (Schultz et al., 1996, supra).

Hence, a need still exists for a method to treat PCNSL with better therapeutic efficacy than the current standard treatment, and with minimal toxicity.

SUMMARY OF THE INVENTION

Accordingly, it is a primary object of the present invention to provide methods for treating individuals having PCNSL.

It is another object of the present invention to provide a method for treating individuals having PCNSL, wherein the method offers a mechanism for achieving better therapeutic efficacy than the current standard therapy for PCNSL.

It is another object of the present invention to provide a method for treating individuals having PCNSL, wherein the method offers a mechanism for achieving better therapeutic efficacy than the current standard therapy for PCNSL, and further offers a mechanism to minimize toxicity to the treated individual.

It is a further object of the present invention to provide a method for treating individuals having PCNSL, wherein the method offers a mechanism for achieving better therapeutic efficacy than the current standard therapy for PCNSL, and further offers a mechanism to minimize toxicity to the treated individual, wherein the method is facilitated by Fas-mediated cytotoxicity of the malignant tumor.

The foregoing objects are based on a novel discovery that primary central nervous system B cell lymphomas, unexpectedly, express significant amounts of Fas on their cell-surface, and further, that ligation (cross-linking) of the receptor on these Fas-bearing tumor cells leads to rapid programmed cell death of the treated tumor. In another embodiment of the present invention, the method comprises combination therapy involving the use of one or more compositions for ligation of Fas expressed by primary central nervous system B cell lymphomas in conjunction with one or more compositions which potentiates or enhances Fas-mediated cytotoxicity of the treated tumor, such as by upregulating the cell-surface expression of Fas by the tumor.

These and further features and advantages of the invention will be better understood from the description of the preferred embodiments when considered in relation to the figures in which:

DETAILED DESCRIPTION OF THE PREFERRED EMBODIMENTS

Definitions

The term "antibody fragment" or "fragment thereof" is used herein, for purposes of the specification and claims, to mean a portion or fragment of an intact antibody molecule, wherein the fragment retains anti-human Fas binding function; i.e., $F(ab')_2$, Fab', Fab, Fv, Fd' and Fd fragments. Methods for producing the various fragments from MAbs are well known to those skilled in the art.

The term "composition which enhances Fas-mediated cytotoxicity" is used herein, for purposes of the specification and claims, to mean a composition that induces increased sensitivity to Fas-mediated cytotoxicity. Such compositions include, but are not limited to, human or recombinant cytokines: interleukin-2 (IL-2), interleukin-1β (IL-1β), interferon-β (IFN-β), gamma interferon (IFN-γ), and tumor necrosis factor α (TNF-α); or a composition such as poly (I)–poly(C), sodium nitroprusside, diphtheria toxin (DTX), adriamycin, and cisplatin.

The term "monoclonal antibody" is used herein, for purposes of the specification and claims, to mean murine monoclonal antibodies, and engineered antibody molecules made therefrom, having agonist anti-human Fas binding function, and further encompasses chimeric or "humanized" antibodies, and as will be more apparent from the following embodiments.

A drawback to systemic therapies is the lack of selectively delivering the therapy to its intended target, diseased tissue, rather than to normal tissue. In that regard, the use of Fas-mediated cytotoxicity of diseased tissue has been complicated by the expression of Fas receptor on normal non-lymphoid tissues such as liver, heart, lung, kidney, and reproductive tissues. For example, injection of anti-Fas antibody into mice systemically results in rapid death due to fulminant liver destruction resulting from massive hepatocyte apoptosis. Other normal tissues were affected as well (Rodriguez et al., 1996, *J. Exp. Med.* 183:1031–6). Thus, it is clear that to induce Fas-mediated cytotoxicity in tumors bearing Fas as a means of treating tumors in patients, it is necessary to find a way to accurately target the treatment to the tumor cells to avoid potential harm to the patient's normal tissues bearing Fas.

The present invention relates to a discovery that primary central nervous system B cell lymphomas, unexpectedly, express significant amounts of Fas on their cell-surface. Importantly, Fas receptor expression is not detected on normal brain parenchyma tissue including astrocytes, neurons, oligo-dendrocytes, microglial or ependymal cells (see, e.g., Leithauser et al., 1993, supra). Further, it is demonstrated herein that cross-linking of the Fas receptor on these Fas-bearing PCNSL cells, such as by agonist anti-Fas antibody, leads to rapid programmed cell death of the treated tumor. The unique anatomical properties of the blood brain barrier allow for the exclusion of high molecular weight, charged particles (e.g., large proteins) from the central nervous system (CNS), thus making the CNS a pharmacologic sanctuary (see, e.g., Bickel et al., 1994, *Bioconjug. Chem.* 5:119–125). Thus, in one embodiment of the present invention, a method for treating a patient having PCNSL comprises introduction into the central nervous system, e.g. intrathecally or intralesionally, of a composition comprising one or more Fas cross-linking molecules that is capable of inducing Fas-mediated cytotoxicity (e.g., agonistic anti-Fas antibody, soluble FasL, or a combination thereof). With an intact blood-brain barrier, such treatment would be targeted to the Fas-bearing CNS tumor cells thereby minimizing toxicity to the patient's normal tissues bearing Fas, such as liver, heart, lung, kidney, and reproductive tissues.

In another embodiment of the present invention, the method of treatment comprises introducing into the patient's central nervous system a combination of therapeutic compositions. The combination therapy involves the use of one or more Fas cross-linking molecules for ligation of Fas expressed by primary central nervous system B cell lymphomas, in conjunction with one or more compositions which potentiates or enhances Fas-mediated cytotoxicity of the treated tumor, such as by upregulating the cell-surface expression of Fas by the tumor.

For purposes of the description, the methods of the present invention will be illustrated in the following examples.

EXAMPLE 1

This Example illustrates various Fas-cross-linking molecules for ligation of Fas on Fas-bearing CNS tumors in the method of the present invention for inducing Fas-mediated cytotoxicity of the treated tumors.

1.1 Agonist anti-Fas antibodies

An agonist anti-Fas antibody is functionally defined as an antibody which, typically, when cross-linking Fas on the cell surface of Fas-bearing cells, induces Fas-mediated cytotoxicity of that cell. Agonist anti-human Fas monoclonal antibodies have been described previously and are commercially available. Such monoclonal antibodies which induce apoptosis of target cells expressing Fas, include, but are not limited to, MAbs M2 and M3 (IgG; Alderson et al., 1995, *J. Exp. Med.* 181:71–77); anti-Fas MAb (IgM; Yonehara et al., 1989, *J. Exp. Med.* 169:1747–1756); MAb CH11 (IgM; Alderson et al., 1994, *Int. Immunol.* 6:1799–806); and anti-APO-1 (IgG; Dhein et al., 1992, *J. Immunol.*, 149:3166–3173). Methods used by those skilled in the art for making agonist anti-human Fas-monoclonal antibodies (including the aforementioned antibodies) involves using isolated and purified human Fas, or Fas-bearing human cells. In either case, the immunogen is used to immunize an animal (such as BALB/c mice) at timed intervals. A few days following the last immunization, spleens from the immunized animal are harvested aseptically, and placed into a tissue culture dish containing tissue culture medium. The primed spleen cells containing B-lymphocytes are mixed with a immunoglobulin non-secreting plasmacytoma cell line (usually a 10:1 to 1:1 ratio) for fusion. Fusion can be accomplished by methods including contacting the cells with a fusion agent such as polyethylene glycol (1 ml of a 50% solution, MW 1400) or by electrofusion. The cells from the fusion are then cloned out in microtiter plate wells. Typically, the plasmacytoma cell line is deficient in an enzyme such as hypoxanthine guanine phosphoribosyl transferase such that fused hybridomas can be selected for by using a tissue culture selection medium such as a medium containing hypoxanthine, aminopterin, and thymidine. The hybridoma cultures are then incubated for several days, under standard tissue culture conditions, before the supernatants are tested for immunoreactivity with human Fas. One of the conventional Fas-mediated cytotoxic assays known to those skilled in the art, and as illustrated in more detail below, may then be used to determine whether the resultant anti-human Fas monoclonal antibody has agonist or antagonist, or neither agonist nor antagonist, properties. Determining immunoglobulin class and isotype may be important in choosing an anti-human Fas monoclonal antibody having desirable or optimal agonist activity, as it has been reported that IgG3 may be the most active isotype, whereas IgG1, IgG2a, and IgA have intermediate activity, and whereas IgG2b lacked detectable activity (Dhein et al., 1992, supra). Additionally, an IgM isotype has advantages in that its pentameric structure allows for the cross linking of Fas in solution (e.g., cerebrospinal fluid); and the large size (e.g., >500 kDa) is much greater than the size exclusion limits of the blood brain barrier, thus making it even more unlikely that such antibody may leak to the peripheral circulation and gain access to organs that do express Fas.

The above-mentioned agonist anti-human Fas-monoclonal antibodies are murine MAbs. Murine monoclonal antibodies (MAbs) or fragments thereof have been used to treat human disease, often with modest to substantial clinical efficacy (see, e.g., Ghetie et al., 1994, *Pharmacol. Ther.* 63:209–34). Studies show that murine MAbs may be repeatedly given on a safe basis, even if a human anti-mouse antibody response develops. Additionally, a human anti-mouse antibody response did not cause significant clinical problems with further repeated infusions of the murine MAb (see, e.g., Frodin et al., 1992, *Cell Biophys*. 21:153–165). It may be appreciated by those skilled in the art that treatment of a patient having PCNSL intrathecally or intralesionally with the method of the present invention is not likely to induce an anti-murine response for at least two reasons. First, such patients are likely to be immunocompromised and thus their ability to mount an immune response may be suppressed. Secondly, although there are limited reports that intrathecal or intrablood-brain barrier synthesis of antibodies could possibly occur, such antibodies are thought to have been raised against invading microbial pathogens (see, e.g., Schwartzman et al., 1994, *Neurology*, 44:1312–6; Smith et al., 1994, *AIDS Res. Hum. Retroviruses* 10:81–9).

However, if an anti-murine response is of a concern to some, an alternative to this embodiment is to modify the murine monoclonal antibodies, such as MAbs M2 and M3, anti-Fas MAb, MAb CH11, and anti-APO-1, can be modified for administration into the patient using techniques standard in the art (e.g., as reviewed by Adair, 1992, *Immunological Reviews* 130: 6–37, herein incorporated by reference). For example, murine monoclonal antibodies may be "humanized" by replacing portions of the murine monoclonal antibody with the equivalent human sequence. In one embodiment, a chimeric antibody is constructed. The construction of chimeric antibodies is now a straightforward procedure (Adair, 1992, supra, at p. 13) in which the chimeric antibody is made by joining the murine variable region to a human constant region. Additionally, chimeric antibodies may be made by joining the hypervariable regions of the murine monoclonal antibody to human constant regions and parts of human variable regions using one of several techniques known in the art. Techniques for constructing chimeric antibodies (murine-human) of therapeutic potential have been described previously (see, e.g., Morrison et al., 1984, *Proc. Natl. Acad. Sci.* 81:6851–6855; Larrick et al., 1991, *Hum. Antibod. Hybridomas* 2:172–189; herein incorporated by reference). Thus, in one embodiment of the present invention, and using methods known in the art, the murine variable region of the agonist anti-human Fas monoclonal antibody is joined to a human constant region to form a chimeric anti-Fas monoclonal antibody having the same specificity and activity as the agonist anti-human Fas monoclonal antibody. In general, humanizing an murine MAb such as by making a chimeric antibody limits the development of human anti-mouse antibody responses. Additionally, the humanized antibodies generally change the pharmacokinetics by providing a longer half-life as compared to the half-life of a murine antibody.

A chimeric MAb can also be constructed using a standard combination of techniques including polymerase chain reaction (PCR) cloning of antibody variable regions, the use of suitable expression vectors already containing the DNA encoding human constant region, insertion of the DNA for the murine MAb variable region into such vector in forming a recombinant vector, and expression of the resultant chimeric antibody by an expression system containing the recombinant vector (See, e.g., Daugherty et al., 1991, *Nucl. Acids Res.* 19:2471–2476; Maeda et al., 1991, *Human Antibodies and Hybridomas* 2:124–134; herein incorporated by reference). One expression vector can be used in which the vector is constructed so that the variable region and constant region genes are in tandem. Alternatively, the DNA encoding the mouse variable region is inserted into one expression vector, and the DNA encoding the human constant region can be inserted into a second expression vector, followed by transfections using both the first and second expression vectors. Expression systems known to those skilled in the art for production of antibody or antibody fragments include mammalian cells (e.g. cell lines such as COS, NSO, or CHO), phage expression libraries, *Escherichia coli*, and yeast (Adair, 1992, supra).

In an additional alternative, a fragment of an agonist anti-human Fas MAb may be produced by methods well known to those skilled in the art (see, e.g., Dhein et al., 1992, supra, herein incorporated by reference). The fragment retains anti-human Fas binding function, and may be selected from the group consisting of F(ab')$_2$, Fab', Fv, Fd' and Fd fragments. It is believed that the fragments, such as Fab fragments, do not appear to penetrate the blood-brain barrier unless modified such as by artificial hydrophobization (Chekhonin et al., 1995, *Neuroreport* 7:129–132). The efficacy of using such fragments, in the method according to the present invention for inducing Fas-mediated cytotoxicity in patients having PCNSL, may be questioned in view of a report that F(ab')$_2$ lack detectable agonist activity (Dhein et al., 1992, supra). These findings indicate that the fragments must exist or be joined in a dimeric or multimeric form to crosslink Fas expressed by the Fas-bearing cell in order to induce Fas-mediated cytotoxicity. Therefore, in one embodiment of the method according to the invention, fragments of an agonist anti-human Fas MAb are used; however, before introduction intrathecally or intralesionally, the fragments are bound together by covalent or noncovalent means to present the fragments in dimeric or multimeric form. Means to bind the fragments together are known to those skilled in the art, and include, but are not limited to the use of a second antibody, protein A, or other joining molecule (see, e.g., Dhein et al., 1992, supra).

1.2 Soluble Fas Ligand

Fas acts as a receptor for Fas-ligand (Fas-L). Human recombinant Fas-L has been produced by using a DNA fragment of murine Fas-L DNA as a probe of a phage library of human CDNA from activated human lymphocytes (Alderson et al., 1995, *J. Exp. Med.* 181:71–77; Takahashi et al., 1994, *Cell* 76:969). Recombinant human Fas-L (rFas-L) so produced has been demonstrated to cross-link Fas on the cell surface of Fas-bearing cells, thereby inducing Fas-mediated cytotoxicity of that cell. Fas-L may also be purified to homogeneity from solubilized membranes of Fas-L bearing human cells, as described previously (Suda et al., 1994, *J. Exp. Med.* 179:873). Thus, in another embodiment of the method according to the present invention for inducing Fas-mediated cytotoxicity in a patient having PCNSL, soluble Fas-L or rFas-L is introduced intrathecally or intralesionally.

EXAMPLE 2

This Example illustrates that primary central nervous system lymphomas, unexpectedly, express significant amounts of cell-surface receptor Fas.

In one illustration of this embodiment, flow cytometric analysis was used to assess Fas expression. Fresh tissue from 2 patients with AIDS- related PCNSL was obtained as residual specimens following pathologic examination. Pathologic examination of all specimens studied revealed B cell lymphoma. Each tissue specimen was then either dispersed to collect single cell suspensions or embedded in cryopreservation media for subsequent immunohistochemical evaluation. Single cell suspensions were analyzed for surface expression of Fas incubating the cell suspension with anti-Fas antibody labelled with fluorescein isothiocyanate (FITC). A portion of each cell suspension was also analyzed for B lymphocyte surface markers by incubating the cells in anti-CD19-FITC and anti-CD20-FITC. FITC-labelled murine isotype control MAbs were used as a control for establishing baseline fluorescence. Co-staining specimens with anti-CD45-FITC allowed gait on lymphoid and non-lymphoid cells in brain biopsy specimens and to evaluate Fas expression on non-lymphoid brain parenchyma. The samples were stained and then analyzed using a flow cytometer using parameters as previously described (Matos et al., 1993, *J. Exp. Med.* 178:1079–1085). The results of flow cytometric analysis of each AIDS-PCNSL specimen revealed that 97.1% of CD20+B cells express Fas (see Table 1), while uninvolved brain parenchyma does not express the pan-B cell marker CD20, nor the Fas antigen.

Figure 1A:
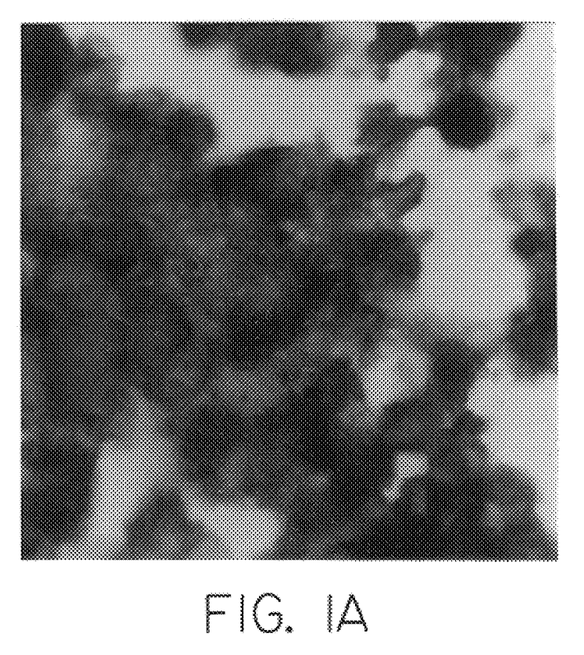
FIG. 1A is a representation showing histochemical staining for human Fas antigen, stained with an anti-human Fas MAb on cells from a biopsy of PCNSL.
Figure 1B:
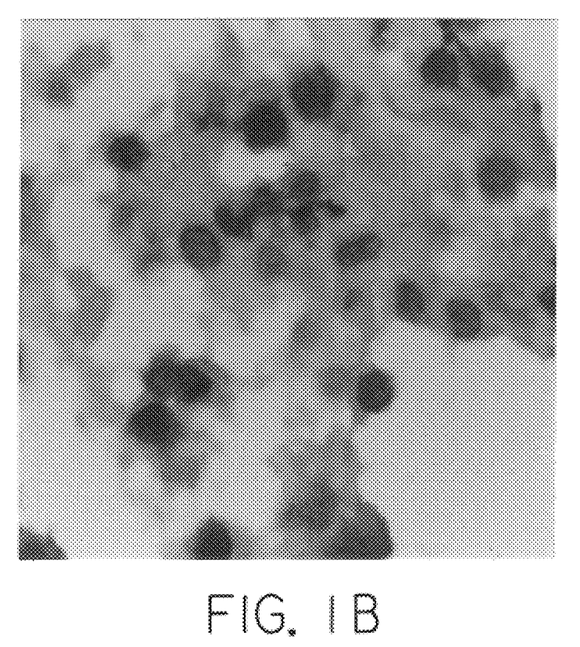
FIG. 1B is a representation showing histochemical staining for human Fas antigen, stained with an isotype control antibody, on cells from a biopsy of PCNSL.

To confirm the results from flow cytometric analysis, six additional AIDS-PCNSL biopsies were analyzed for Fas expression by immunohistochemical staining. For immunohistochemical analysis, tissue specimens embedded in cryopreservation media were frozen in liquid nitrogen. Five micrometer sections for surface antigen staining were placed on silicone-coated slides and were fixed for 5 minutes in −20° C. acetone. 0.1saponin was included in all solutions and washes when staining with anti-Fas MAb or the mouse isotype MAb control. Following 3 washes in balanced salt buffer, all sections were blocked in 100 ml avidin-blocking solution for 15 minutes. Then, the sections were incubated in biotin blocking solution for 15 minutes, followed by incubation in 0.2 M sodium azide and 1.0% $H_2O_2$ in balanced salt solution for 30 minutes, and a solution containing 500 mg/ml goat IgG for 30 minutes. Primary MAbs were then added, and sections were incubated overnight at 4° C. MAbs used in staining the sections included: anti-CD19 specific for a human B lymphocyte surface marker; and M2, M3, and M31 specific for the human Fas receptor. A murine isotype control (IgG1) MAb was used as a control for each section to establish background staining. Sections were then washed 3 times with balanced salt buffer, blocked with 10% goat serum for 30 minutes, washed 3 times again, and incubated with a secondary biotin-conjugated anti-mouse IgG1 MAb for 30 minutes at room temperature and washed again. One hundred μl of avidin-horseradish peroxidase conjugate was next added to each section for 30 minutes, the sections washed, allowed to dry for 2 minutes, then reacted with 100 ml DAB peroxidase substrate solution for 10 minutes. Slides were submerged in $ddH_2O$ for 1 minute, counter-stained with hematoxylin, and covered slipped for mounting. The results of the immunohistochemical staining of AIDS-PCNSL biopsies are summarized in FIG. 1A showing abundant amounts of Fas expressed on the cell-surface of PCNSL cells. FIG. 1B shows the lack of staining on these cells when incubated with an isotype control antibody.

The results of the flow cytometric analysis ("FACS"), and immunohistochemical staining ("IHC"), of AIDS-PCNSL biopsies for Fas antigen are summarized in Table 1; wherein the # of samples=number of samples testing positive/total number of samples analyzed, and wherein+++=between 90%–100% reactivity.

TABLE 1

| Tumor | # of samples | Expression | Method |
|---|---|---|---|
| AIDS-PCNSL | 2/2 | +++ | FACS |
| AIDS-PCNSL | 6/6 | +++ | IHC |

Taken together, flow cytometric analysis and immunohistochemical staining analysis show that primary central nervous system lymphomas, isolated from AIDS patients, demonstrate abundant surface expression of Fas antigen.

EXAMPLE 3

This Example illustrates that primary central nervous system lymphomas which unexpectedly express significant amounts of cell-surface receptor Fas, are susceptible to Fas-mediated cytotoxicity induced by a Fas-cross-linking molecule. As mentioned above, one skilled in the art would appreciate that just because a cell, such as those of PCNSL associated with AIDS, may bear Fas antigen does not necessarily confer sensitivity of that cell to anti-Fas mediated cytotoxicity. In fact, cells of Kaposi's sarcoma, the most common malignancy associated with AIDS, express cell-surface Fas but are resistant to induction of Fas-mediated cytotoxicity after treatment with agonist anti-Fas antibody (MAb CH-11; Mori et al., 1996, *Cancer Res.* 56:1874–9).

The method for assessing Fas-mediated cytotoxicity is a DNA fragmentation assay used to detect apoptosis. The PCNSL tumor cells suspensions were plated into 1 ml wells with culture medium supplemented with serum in the presence or absence of different anti-human Fas MAbs. Anti-human Fas MAbs M2 and M3, when immobilized, will induce apoptosis of Fas-bearing target cells. The anti-human Fas MAbs, and the isotype control MAb, were immobilized by coating flat bottom wells. Excess soluble MAbs M2 and M3 competitively block the induction of apoptosis by the immobilized MAbs M2 and M3. In contrast, the anti-human Fas MAb M31 will bind Fas antigen, but will not induce an apoptotic signal following immobilization and ligation to Fas on Fasbearing target cells. For analysis of Fas-mediated cytotoxicity, tumor cells were cultured with immobilized anti-human Fas MAbs (M3 at 10 µg/ml) in the absence or presence of a 5-fold excess of soluble M3 MAbs, and harvested at various time points to determine the extent of apoptosis by either light microscopy or cytospin preparations, flow cytometric analysis of propidium iodide-stained nuclei, or gel electrophoresis, using methods and parameters previously described (Cascino et al., 1996, *J. Immunol.* 156:1317). Briefly, DNA labeling by propidium iodide was performed by fixing the cells in 70% ethanol, treating the fixed and washed cells with RNAse, incubating the cells in propidium iodide, and measuring the propidium iodide fluorescence of individual apoptotic cell nuclei using flow cytometry. For DNA electrophoresis, the DNA was isolated, extracted, precipitated, resuspended, loaded onto and electrophoresed in an agarose gel, and viewed by ethidium bromide staining. Using these methods with a anti-Fas MAb of IgM isotype, the antibody need not be immobilized as this isotype can induce apoptosis in solution.

Figure 2A:
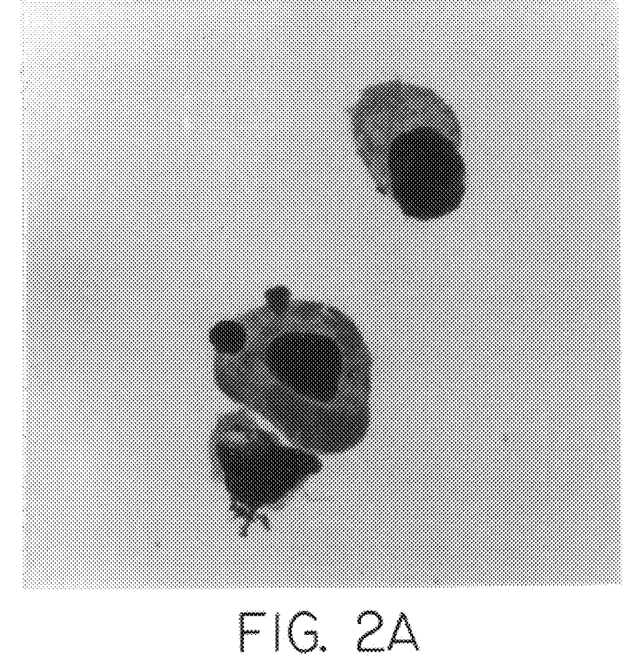
FIG. 2A shows the morphologic characteristics of PCNSL cells undergoing apoptosis after binding with an anti-human Fas MAb.
Figure 2B:
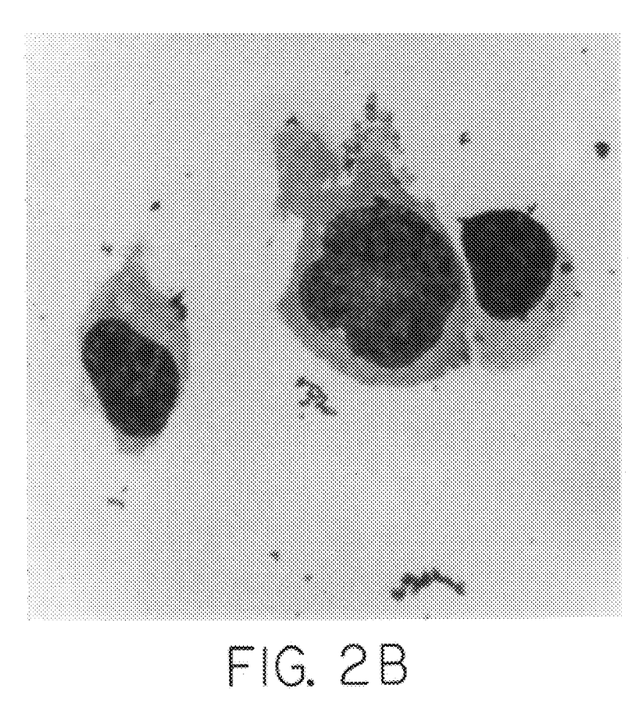
FIG. 2B shows normal lymphoblastoid phenotype of PCNSL cells where apoptosis is blocked.

Tumor cell preparations from AIDS-PCNSL biopsies, following overnight incubation in the presence of immobilized anti-human FAS M3 MAb and staining with propidium iodide, showed morphological characteristics of apoptosis including hypodiploid DNA representing DNA fragmentation that characterizes apoptosis (FIG. 2A). In contrast, normal lymphoblastoid phenotype is observed when the same cells are incubated in the presence of both soluble MAb M3 and immobilized MAb M3 (FIG. 2B). 57% of AIDS-PCNSL cells were found within the hypodiploid fraction following exposure to either immobilized M2 or M3 MAbs, while only 19% of such cells were within the hypodiploid fraction following exposure to either immobilized M2 or M3 MAbs in the presence of an excess of the respective soluble anti-Fas MAb. All preparations were shown to consist of >90% B lymphocyte origin as determined by immunostaining with anti-human CD19-PE and flow cytometric analysis.

Figure 3:
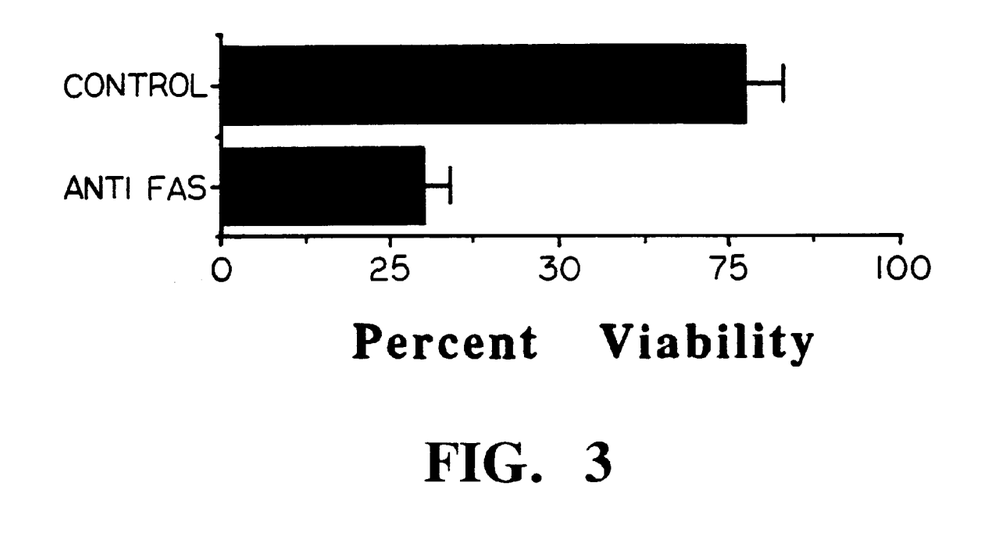
FIG. 3 is a bar graph showing percent viability of PCNSL cells after various treatment protocols.

For analysis by light microscopy, the tumor cells from patients with AIDS-PCNL were analyzed for viability by vital dye exclusion (an indicator of loss of membrane integrity) and using a hemocytometer. Cells were enumerated from two wells under each experimental condition, and values were expressed as mean percent ± standard error of the mean. As shown in FIG. 3, in a vital dye exclusion assay and after a 24 hour incubation with immobilized anti-Fas M3 MAb the AIDS PCNL tumor cells displayed substantial cell death ("Anti-Fas"), as compared to the same tumor cell samples which were co-incubated with soluble MAb M3 and immobilized MAb M3 ("Control"). Fas-mediated apoptosis of tumors from AIDS-PCNL was further confirmed by morphological evaluation using cytospin preparations using techniques known in the art (Baiocchi et al., 1995, *Blood* 85:1603). Morphological features of apoptosis (e.g., nuclear degradation and membrane blebbing) were consistently observed in the majority of tumor cells after only a 2 hour incubation with immobilized MAb M3; whereas normal lymphoblastoid morphology was observed in the majority of cells co-incubated with soluble MAb M3 and immobilized MAb M3.

Thus, in one embodiment of the method according to the present invention for inducing Fas-mediated cytotoxicity of PCNSL cells, a therapeutically effective amount of one or more Fas-cross-linking molecules is introduced intrathecally or intralesionally into the patient having PCNSL. For purposes of illustration, but not limitation, typically $10^5$–$10^6$ Fas-bearing target cells are incubated with about 0.1 µg to about 10 µg of agonist anti-human Fas MAb for inducing Fas-mediated cytotoxicity. However, it will be appreciated by those skilled in the art that therapeutically effective amounts of the Fas-cross-linking composition for treating a patient having PCNSL will depend on the mode of administration, tumor burden of the patient, dose schedule, patient's age, size and other background factors. It will also be appreciated by those skilled in the art that the Fas-cross-linking composition may further comprise a pharmaceutically acceptable carrier medium (e.g., including buffered aqueous solutions such as phosphate buffers, buffered salines; alcoholic/aqueous solutions; and emulsions or suspensions; wherein the ionic strength, pH, and other properties of the pharmaceutically acceptable carrier may be adjusted to maximize delivery and activity of the composition to that site).

EXAMPLE 4

This Example illustrates an embodiment of the method that primary central nervous system lymphomas which unexpectedly express significant amounts of cell-surface receptor Fas, and are susceptible to Fas-mediated cytotoxicity induced by a Fas-cross-linking molecule, may be made additionally sensitive to Fas-mediated cytotoxicity by contacting the Fas-bearing cells to at least one composition which enhances Fas-mediated cytotoxicity. One such composition that induces in PCNSL cells an increased sensitivity to Fas-mediated cytotoxicity is interleukin-2 (IL-2).

This embodiment of the method of the present invention to induce Fas-mediated cytotoxicity of PCNSL in vivo, involves combination therapy using (a) one or more Fas-cross-linking compositions; and (b) IL-2. While not relating directly to Fas antigen expression or Fas-mediated cytotoxicity, but concerning IL-2 treatment of tumors in the central nervous system, it has been reported that treatment of such tumors intralesionally with large amounts of IL-2 resulted in central nervous system toxicity caused in part by vasogenic brain edema (Tjuvajev et al., 1995, *Cancer Res.* 55:1902–10. As related to Fas-mediated cytotoxicity, Fas-mediated apoptosis could be prevented in T cells by treatment with IL-2 (Estaquier et al., 1996, *Blood* 87:4959–66). Thus, it was an unexpected result in the development of the method of the present invention that a low dose (e.g. 1–100 ng/ml) of IL-2 appears to enhance Fas expression in PCNSL cells, and further enhances their susceptibility to Fas-mediated cytotoxicity induced by a Fas-cross-linking composition. In that regard, a method comprising treatment of a patient having PCNSL with combination intrathecal or intralesional therapy using a low dose of IL-2 in conjunction with a Fas-cross-linking composition (a) allows the clinician the option to reduce the concentration of the Fas-cross-linking composition used while still maintaining therapeutic efficacy; and (b) minimizes the possibility of CNS toxicity observed in treatment with high doses of IL-2.

Using the methods illustrated in Example 2, single cell suspensions of primary central nervous system lymphoma tissue were analyzed by flow cytometry for expression of cell-surface receptor Fas. These data were compared to data generated from cell suspensions which were first incubated with IL-2 (added to 10 ng/ml) for 96 hours prior to harvesting and analysis for Fas expression by flow cytometry. Preincubation of PCNSL cells with a low dose of IL-2 resulted in a marked upregulation of cell-surface Fas expression on PCNSL cells (64% more expression than cells not preincubated with IL-2).

Using the methods illustrated in Example 3 for assessing Fas-mediated cytotoxicity by a DNA fragmentation assay, primary central nervous system lymphoma tissue cells were analyzed for Fas-mediated cytotoxicity induced by treatment with an agonist anti-human Fas MAb (M2 or M3) and compared to Fas-mediated cytotoxicity generated from cell suspensions which were first incubated with IL-2 (added to 10 ng/ml) for 96 hours prior to treatment with the Fas-cross-linking composition and analysis for Fas-mediated cytotoxicity. Preincubation of PCNSL cells with a low dose of IL-2 resulted in a marked potentiation (50% more) Fas-mediated cytotoxicity as compared to tumor cells without pretreatment with IL-2. Further, IL-2 has additional advantages including that it is also capable of inducing the expression of Fas-L on activated T cells and activated natural killer cells.

Thus, in another embodiment of the method according to the present invention for inducing Fas-mediated cytotoxicity of PCNSL cells, a combination therapy is used. The combination therapy comprises the steps of treating a patient having PCNSL with a therapeutically effective low dose of IL-2 administered intrathecally or intralesionally. Following the administration of the low dose of IL-2, a therapeutically effective amount of one or more Fas-cross-linking compositions is introduced into the patient intrathecally or intralesionally to induce the Fas-mediated cytotoxicity. For purposes of illustration, but not limitation, typically the therapeutically effective amount of the one or more Fas-cross-linking compositions is introduced approximately 1–5 days following administration of the low dose of IL-2. It will be appreciated by those skilled in the art that therapeutically effective amounts of the Fas-cross-linking composition and IL-2 for treating a patient having PCNSL with this combined therapy will depend on the mode of administration, tumor burden of the patient, dose schedule, patient's age, size and other background factors. It will also be appreciated by those skilled in the art that the Fas-cross-linking composition and the IL-2 each may further comprise a pharmaceutically acceptable carrier medium.

EXAMPLE 5

This Example illustrates another embodiment of the method of combined therapy against primary central nervous system lymphomas. The combination therapy comprises the steps of treating a patient having PCNSL with a therapeutically effective amount of at least one composition which enhances Fas-mediated cytotoxicity in conjunction with a therapeutically effective amount of at least one Fas-cross-linking composition. Compositions which enhance Fas-mediated cytotoxicity include, but are not limited to, human or recombinant cytokines: interleukin-2 (IL-2), interleukin-1β (IL-1β), interleukin-10 (IL-10), interferon-β (IFN-β), gamma interferon (IFN-γ), and tumor necrosis factor α (TNF-α); or a composition such as poly (l)–poly(C), sodium nitroprusside, diphtheria toxin (DTX), adriamycin, and cisplatin.

For example, using the methods illustrated in Example 4, single cell suspensions of primary central nervous system lymphoma tissue were analyzed by flow cytometry for expression of cell-surface receptor Fas. These data were compared to data generated from cell suspensions which were first incubated with either IL-10 (added to 50 ng/ml) or IFN-γ (10 ng/ml) for 96 hours prior to harvesting and analysis for Fas expression by flow cytometry. The results show that preincubation of PCNSL cells with IL-10 or IFNγ resulted in a marked upregulation (38% more with IL-10; and 42% more with IFN-γ) than observed in cells not preincubated with the respective cytokines. These results are consistent with the findings that IFN-γ upregulates expression of cell-surface Fas and Fas-mediated cytotoxicity in other cell types (Oyaizu et al., 1994, Blood 84:2622–2631; Weller et al., 1995, Cancer Res. 55:2936–44; Yonehara et al., 1989, supra; Quirk et al., 1995, Biol. Reprod. 52:279–287; and Takahashi et al., 1995, J. Invest. Dermatol., 1995, 105:810–5). Other cytokines have been reported to have a similar effect on various cell types; i.e. upregulate Fas cell-surface expression thereby increasing the susceptibility of the Fas-bearing cell to Fas-mediated cytotoxicity. These cytokines include TNF-α (e.g., 25 ng/ml; Lens et al., 1996, J. Immunol. 156:507–514; Weller et al., 1995, supra; and Yonehara et al., 1989, supra); and IL-1β (Weller et al., 1995, supra.).

Thus, in another embodiment of the method according to the present invention for inducing Fas-mediated cytotoxicity of PCNSL cells, a combination therapy is used. The combination therapy comprises the steps of treating a patient having PCNSL with a therapeutically effective low dose of at least one cytokine selected from the group consisting of IL-2, IL-10, IL-1β, IFN-γ, and TNF-α, administered intrathecally or intralesionally. Following the administration of the low dose of cytokine, a therapeutically effective amount of one or more Fas-cross-linking compositions is introduced into the patient intrathecally or intralesionally to induce the Fas-mediated cytotoxicity. For purposes of illustration, but not limitation, typically the therapeutically effective amount of the one or more Fas-cross-linking compositions is introduced 2–5 days following administration of the low dose of cytokine. It will be appreciated by those skilled in the art that therapeutically effective amounts of the Fas-cross-linking composition and cytokine for treating a patient having PCNSL with this combined therapy will depend on the mode of administration, tumor burden of the patient, dose schedule, patient's age, size and other background factors. It will also be appreciated by those skilled in the art that the Fas-cross-linking composition and the cytokine each may further comprise a pharmaceutically acceptable carrier medium.

In another embodiment of the method according to the present invention of combination therapy for inducing Fas-mediated cytotoxicity of PCNSL cells, the tumor is pretreated with diphtheria toxin. Diphtheria toxin has been shown to upregulate Fas cell-surface expression thereby synergistically increasing the susceptibility of the Fas-bearing cell to Fas-mediated cytotoxicity (Morimoto, 1993, Cancer Res. 53:2591–6). The combination therapy comprises the steps of treating a patient having PCNSL with a therapeutically effective of diphtheria toxin administered intrathecally or intralesionally. Following the administration of the toxin, a therapeutically effective amount of one or more Fas-cross-linking compositions is introduced into the patient intrathecally or intralesionally to induce the Fas-mediated cytotoxicity. For purposes of illustration, but not limitation, typically the therapeutically effective amount of the one or more Fas-cross-linking compositions is introduced 2–5 days following administration of the toxin. It will be appreciated by those skilled in the art that therapeutically effective amounts of the Fas-cross-linking composition and toxin for treating a patient having PCNSL with this combined therapy will depend on the mode of administration, tumor burden of the patient, dose schedule, patient's age, size and other background factors. It will also be appreciated by those skilled in the art that the Fas-cross-linking composition and the toxin each may further comprise a pharmaceutically acceptable carrier medium.

In another embodiment of the method according to the present invention of combination therapy for inducing Fas-mediated cytotoxicity of PCNSL cells, one or more chemotherapeutic agents is used to sensitize the tumor. Using one or more chemotherapeutic agents has been shown to upregulate Fas cell-surface expression thereby synergistically increasing the susceptibility of the Fas-bearing cell to Fas-mediated cytotoxicity (Morimoto, 1993, supra; and Uslu et al., 1996, *Gynecol. Oncol.* 62:282–291). The combination therapy comprises the steps of treating a patient having PCNSL with a therapeutically effective amount of at least one chemotherapeutic agent selected from the group consisting of adriamycin, cisplatin, cyclophosphamide, doxorubicin, and dexamethasone. While the one or more chemotherapeutic agents can be administered to the patient by standard routes of administration such as intravenously, high doses of the chemotherapeutic agents are needed to get therapeutically effective amounts across the blood-brain barrier. Thus to avoid using such high doses, and to minimize possibility of systemic toxicity associated therewith, it may be desirable to administer to the patient the one or more chemotherapeutic agents intrathecally or intralesionally. Following the administration of the one or more chemotherapeutic agents, a therapeutically effective amount of one or more Fas-cross-linking compositions is introduced into the patient intrathecally or intralesionally to induce the Fas-mediated cytotoxicity. For purposes of illustration, but not limitation, typically the therapeutically effective amount of the one or more Fas-cross-linking compositions is introduced 2–5 days following administration of the one or more chemotherapeutic agents. It will be appreciated by those skilled in the art that therapeutically effective amounts of the Fas-cross-linking composition and chemotherapeutic agents for treating a patient having PCNSL with this combined therapy will depend on the mode of administration, tumor burden of the patient, dose schedule, patient's age, size and other background factors. It will also be appreciated by those skilled in the art that the Fas-cross-linking composition and the chemotherapeutic agents each may further comprise a pharmaceutically acceptable carrier medium.

In another embodiment of the method according to the present invention of combination therapy for inducing Fas-mediated cytotoxicity of PCNSL cells, poly(l)–poly(C) is used to sensitize the tumor. Poly(l)–poly(C), a synthetic double-stranded RNA has been shown to upregulate Fas cell-surface expression thereby synergistically increasing the susceptibility of the Fas-bearing cell to Fas-mediated cytotoxicity (100 $\mu$g/ml; Takenori, 1995, *Virology* 209:288–296). The combination therapy comprises the steps of treating a patient having PCNSL with a therapeutically effective amount of poly(l)–poly(c) intrathecally or intralesionally. Following the administration of the poly(l)–poly(C), a therapeutically effective amount of one or more Fas-cross-linking compositions is introduced into the patient intrathecally or intralesionally to induce the Fas-mediated cytotoxicity. For purposes of illustration, but not limitation, typically the therapeutically effective amount of the one or more Fas-cross-linking compositions is introduced about 6 hours to 4 days following administration of the poly(l)–poly(C). It will be appreciated by those skilled in the art that therapeutically effective amounts of the Fas-cross-linking composition and poly(l)–poly(C) for treating a patient having PCNSL with this combined therapy will depend on the mode of administration, tumor burden of the patient, dose schedule, patient's age, size and other background factors. It will also be appreciated by those skilled in the art that the Fas-cross-linking composition and the poly(l)–poly(C) each may further comprise a pharmaceutically acceptable carrier medium.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method of reducing the growth of primary central nervous system lymphoma cells in an individual by inducing the lymphoma cells to undergo Fas-mediated cytoxicity, said method comprising administering intrathecally or intralesionally a therapeutically effective amount of at least one Fas-cross-linking composition selected from the group consisting of an agonist anti-human Fas monoclonal antibody or anti-human Fas bid fragments thereof, soluble Fas-ligand (Fas-L), and a combination thereof.

2. The method according to claim 1, wherein the Fas-cross-linking composition further comprises a pharmaceutically acceptable carrier.

3. The method according to claim 1, wherein the fragments are selected from the group consisting of $F(ab')_2$, Fab', Fab, Fv, Fd' and Fd, and wherein said fragments are joined in forming dimeric or multimeric molecules that cross-link Fas expressed on the cell-surface of the lymphoma cells.

4. The method according to claim 1, wherein the Fas-cross-linking composition comprises an agonist anti-human Fas monoclonal antibody.

5. The method according to claim 4, wherein the agonist anti-human Fas monoclonal antibody is a chimeric antibody comprising a murine variable region and a human constant region.

6. The method according to claim 1, wherein the Fas-cross-linking composition comprises Fas-L.

7. A method of combination therapy for treating a primary central nervous system lymphoma in an individual by inducing the lymphoma cells to undergo Fas-mediated cytotoxicity, said method comprises administering intrathecally or intralesionally in sequential order a therapeutically effective amount of:

(a) at least one composition which enhances Fas-mediated cytotoxicity; and (b) at least one Fas-cross-linking composition selected from the group consisting of an agonist anti-human Fas monoclonal antibody or fragments thereof, soluble Fas-ligand (Fas-L), and a combination thereof;

wherein pretreatment with the at least one composition which enhances Fas-mediated cytotoxicity sensitizes the pretreated lymphoma cells to Fas-mediated cytotoxicity induced by subsequent treatment with the at least one Fas-cross-linking composition.

8. The method according to claim 7, wherein the Fas-cross-linking composition further comprises a pharmaceutically acceptable carrier.

9. The method according to claim 7, wherein the composition which enhances Fas-mediated cytotoxicity further comprises a pharmaceutically acceptable carrier.

10. The method according to claim 7, wherein the composition which enhances Fas-mediated cytotoxicity is a cytokine selected from the group consisting of IL-2, IL-10, IL-1$\beta$, IFN-$\gamma$, and TNF-$\alpha$, wherein the cytokine is administered intrathecally or intralesionally.

11. The method according to claim 10, wherein the cytokine is administered about 2 to about 5 days prior to administration of the Fas-cross-linking composition.

12. The method according to claim 7, wherein the composition which enhances Fas-mediated cytotoxicity is diphtheria toxin administered intrathecally or intralesionally.

13. The method according to claim 12, wherein the diphteria toxin is administered about 2 to about 5 days prior to administration of the Fas-cross-linking composition.

14. The method according to claim 7, wherein the composition which enhances Fas-mediated cytotoxicity is at least one chemotherapeutic agent selected from the group consisting of adriamycin, cisplatin, cyclophosphamide, doxorubicin, and dexamethasone.

15. The method according to claim 14, wherein the at least one chemotherapeutic agent is administered intrathecally or intralesionally.

16. The method according to claim 14, wherein the at least one chemotherapeutic agent is administered about 2 to about 5 days prior to administration of the Fas-cross-linking composition.

17. The method according to claim 7, wherein the composition which enhances Fas-mediated cytotoxicity is poly(l)–poly(C) administered intrathecally or intralesionally.

18. The method according to claim 17, wherein the poly(l)–poly(C) is administered about 6 hours to about 4 days prior to administration of the Fas-cross-linking composition.

19. The method according to claim 7, wherein the fragments are selected from the group consisting of F(ab')$_2$, Fab', Fab, Fv, Fd' and Fd, and wherein said fragments are joined in forming dimeric or multimeric molecules that cross-link Fas expressed on the cell-surface of the lymphoma cells.

20. The method according to claim 7, wherein the Fas-cross-linking composition comprises an agonist anti-human Fas monoclonal antibody.

21. The method according to claim 20, wherein the agonist anti-human Fas monoclonal antibody is a chimeric antibody comprising a murine variable region and a human constant region.

22. The method according to claim 7, wherein the Fas-cross-linking composition comprises Fas-L.

* * * * *

UNITED STATES PATENT AND TRADEMARK OFFICE
CERTIFICATE OF CORRECTION

PATENT NO. : 6,042,826
DATED : 3/28/00
INVENTOR(S) : Caligiuri et al.

It is certified that error appears in the above-identified patent and that said Letters Patent is hereby corrected as shown below:

Col. 14, line 18 - "bid" should be -- binding --.

Signed and Sealed this

Twentieth Day of February, 2001

Attest:

NICHOLAS P. GODICI

Attesting Officer

Acting Director of the United States Patent and Trademark Office